United States Patent
Shinoda et al.

(10) Patent No.: US 12,429,190 B2
(45) Date of Patent: Sep. 30, 2025

(54) ULTRAVIOLET RADIATION APPARATUS

(71) Applicant: SHIKOH TECH CO., LTD., Awaji (JP)

(72) Inventors: Tsutae Shinoda, Akashi (JP); Hitoshi Hirakawa, Takasago (JP); Kenji Awamoto, Miki (JP); Takefumi Hidaka, Kobe (JP); Junichiro Takahashi, Nishinomiya (JP); Tetsuya Makino, Kakogawa (JP); Masayuki Wakitani, Akashi (JP); Yoko Shinoda, Akashi (JP)

(73) Assignee: SHIKOH TECH CO., LTD., Awaji (JP)

( * ) Notice: Subject to any disclaimer, the term of this patent is extended or adjusted under 35 U.S.C. 154(b) by 168 days.

(21) Appl. No.: 18/001,187

(22) PCT Filed: Nov. 22, 2021

(86) PCT No.: PCT/JP2021/042827
§ 371 (c)(1),
(2) Date: Dec. 8, 2022

(87) PCT Pub. No.: WO2022/113943
PCT Pub. Date: Jun. 2, 2022

(65) Prior Publication Data
US 2023/0258315 A1    Aug. 17, 2023

(30) Foreign Application Priority Data
Nov. 24, 2020  (JP) ................. 2020-194593

(51) Int. Cl.
*F21V 9/06*     (2018.01)
*A61L 2/10*     (2006.01)
*A61L 2/20*     (2006.01)

(52) U.S. Cl.
CPC .................... *F21V 9/06* (2013.01); *A61L 2/10* (2013.01); *A61L 2/20* (2013.01)

(58) Field of Classification Search
CPC ............... F21V 9/06; A61L 2/10; A61L 2/20
See application file for complete search history.

(56) References Cited

U.S. PATENT DOCUMENTS

2009/0315440 A1* 12/2009 Makino ............... H01J 11/18
                                                        313/1
2011/0227501 A1   9/2011 Awamoto et al.
(Continued)

FOREIGN PATENT DOCUMENTS

JP    H04-2001 A      1/1992
JP    2011-193929 A   10/2011
(Continued)

OTHER PUBLICATIONS

Japan Patent Office, International Search Report issued in corresponding Application No. PCT/JP2021/042827, mailed Jan. 25, 2022.

*Primary Examiner* — Nicole M Ippolito
(74) *Attorney, Agent, or Firm* — Stites & Harbison, PLLC; Jeffrey A. Haeberlin (57) ABSTRACT

The present invention provides a deep ultraviolet radiation apparatus that is safe and has a high bacteria eliminating effect.
The ultraviolet radiation apparatus comprises an optical filter that prevents the transmission of ultraviolet light of 240 nm or more emitted from a phosphor, wherein the optical filter is arranged facing light emitting surfaces of a gas-discharging tube array-type surface-emitting ultraviolet light source device comprising phosphor layer having a broad emission spectrum with a wavelength width of at least 210 nm to 250 nm with a peak wavelength of 228 nm. Light irradiated from the light source device is incident on a filter
(Continued)

membrane with an incident angle thereof being altered by a transparent substrate of the optical filter. An ozone generation space may be formed between the surface-emitting ultraviolet light source device and the optical filter.

20 Claims, 10 Drawing Sheets

(56) References Cited

U.S. PATENT DOCUMENTS

| | | |
|---|---|---|
| 2017/0186596 A1 | 6/2017 | Shinoda et al. |
| 2020/0234941 A1 | 7/2020 | Yagyu et al. |
| 2021/0139774 A1 | 5/2021 | Nobutsugu et al. |
| 2022/0231212 A1* | 7/2022 | Yasuda .................. H01L 24/05 |

FOREIGN PATENT DOCUMENTS

| | | |
|---|---|---|
| JP | 2014-058612 A | 4/2014 |
| JP | 2015-193521 A | 11/2015 |
| JP | 2018-114197 A | 7/2018 |
| JP | 2018-190686 A | 11/2018 |
| JP | 2019-017808 A | 2/2019 |
| WO | 2016/125708 A1 | 8/2016 |
| WO | 2018/235723 A1 | 12/2018 |

* cited by examiner

ULTRAVIOLET RADIATION APPARATUS

TECHNICAL FIELD OF THE INVENTION

The present invention relates to an ultraviolet radiation apparatus, and more particularly to a deep ultraviolet radiation apparatus configured to eliminate viruses and various bacteria (including disinfection and sterilization) and deodorize. In the present invention, deep ultraviolet rays mean radiation in an ultraviolet region in a range of wavelengths from 200 nm to 300 nm; and among these, the deep ultraviolet rays having a peak wavelength of around 228 nm will be referred to as UVC1, and the deep ultraviolet rays having a peak wavelength of around 260 nm will be referred to as UVC2. Vacuum ultraviolet (VUV) means ultraviolet rays having wavelengths of 200 nm or less generated by noble gas discharge.

BACKGROUND OF THE INVENTION

The bacteria elimination effects and the deodorization effects of ultraviolet rays have been traditionally well known, and various bacteria elimination or disinfection devices using ultraviolet irradiation have been known (see, for example, PTL 1 to PTL 4). The below-listed PTL 1 mentions that ultraviolet rays with wavelengths of 200 to 230 nm are beneficial for virus inactivation and optimal as not affecting human cells. In a device disclosed in PTL 1, an excimer lamp having a narrow peak wavelength of 222 nm is mentioned as a typical example of a light source that emits deep ultraviolet light in the above wavelength range.

CROSS REFERENCES

Patent Literature Documents

PTL 1: National Publication of Japanese Translation of PCT Application No. 2014-58612
PTL 2: PCT International Publication No. WO 2016/125708
PTL 3: Japanese Unexamined Patent Application Publication No. 2015-193521
PTL 4: PCT International Publication No. WO 2018/235723

SUMMARY OF THE INVENTION

Object of the Invention

However, the excimer lamp that emits deep ultraviolet rays with the wavelength of 222 nm uses krypton chloride (KrCl), which is highly toxic, as a discharge gas; and when this lamp is broken, environmental problems would inevitably occur. The KrCl excimer has a narrow emission wavelength width and thus has a problem that the excimer can limitedly inactivate bacteria and viruses. Namely, even though more efficient inactivation ability can be expected in the shorter wavelength region than 222 nm, this excimer lamp cannot be used because the emission wavelength thereof is limited to about 222 nm.

In a conventional surface-emitting ultraviolet light source device for disinfection disclosed in PTL2, a UVC2 light source device with peak wavelengths exclusively in the vicinity of 260 nm was the limit of commercialization due to limitations in a glass material (traditional material) for gas-discharging tubes and limitations in a phosphor material. Since short wavelengths of around 240 nm are absorbed by the glass material used for tube envelopes in the UVC2 light source device, it has been desired to develop a new glass material that transmits shorter wavelengths of deep ultraviolet light, which is expected to have a high disinfection effect against viruses and bacteria. It was also necessary to develop a new process for emitting the shorter wavelengths of the deep ultraviolet light from a new phosphor with appropriate luminescence efficiency.

The present invention solves the above problems and provides a deep ultraviolet radiation apparatus that has broad elimination effects on many viruses and bacteria and yet is safe and has minimal impact on the human body.

BEST MODE FOR CARRYING OUT THE INVENTION

The ultraviolet radiation apparatus of the present invention that solves the above problems is based on a gas-discharging tube array-type surface-emitting light source device that utilizes a deep ultraviolet phosphor as a deep ultraviolet light source, unlike conventional devices that emit from excimer lamps wavelengths in the vicinity of 222 nm, which are considered beneficial for bacterial inactivation. The conventional gas-discharging tube array-type surface-emitting deep ultraviolet light source devices themselves have been already known as disclosed in the above-mentioned PTL2 and others. However, the present invention is characterized by using a deep ultraviolet phosphor layer that is excited by a discharge of xenon gas (Xe) and has a broad emission spectrum (UVC1) in a wavelength range of at least 210 to 250 nm with a peak wavelength in the vicinity of 228 nm, and also characterized by arranging an optical filter that is placed opposite to light emitting surfaces (which are surfaces of gas-discharging tubes arrayed), as needed, and substantially blocks the transmission of ultraviolet rays in a wavelength region of 240 nm or more of the phosphor emission spectrum.

The optical filter of the present invention is made of a dielectric multilayer filter formed on a surface of an ultraviolet permeable substrate, and the ultraviolet permeable substrate is configured to face the light emitting surfaces of the surface-emitting ultraviolet source device. The ultraviolet permeable substrate functions to regulate incident angles of radiant light from the light emitting surfaces to the dielectric multilayer filter.

The present invention is characterized by another aspect: A surface-emitting ultraviolet light source device is used that comprises a gas-discharging tube array that is capable of actively emitting vacuum ultraviolet VUV emitted from 172 nm Xe and also capable of efficiently emitting UVC1 simultaneously, by selecting new UV permeable glass, as a glass material forming envelopes of gas-discharging tubes, that can extract vacuum UV light to the outside. Therefore, this aspect of the present invention has the following feature of the ultraviolet radiation apparatus: An ozone generation space is formed between the light emitting surfaces of the surface-emitting light source device, which emit VUV and UVC1 simultaneously, and the optical filter; and ozone generated in this space is released into an environmental space.

As yet another aspect, the present invention provides an ultraviolet radiation apparatus in which the thickness of the glass tubes forming the envelopes of the gas-discharging tubes is adjusted in such a way as to limit the emission of the UV light generated inside the tubes on the short wavelength side, while the optical filter placed opposite the light emitting surfaces allows for the limitation on the emission of the UV light on the long wavelength side. This configuration enables a design of the apparatus that widely encompasses a range of wavelengths from 200 nm to 250 nm, which are expected to be most effective for disinfection and bacteria elimination, and prevents the radiation of ultraviolet rays in a vacuum ultraviolet region and of ultraviolet rays in a deep ultraviolet region with wavelengths of 240 nm or longer, which are harmful to the human body.

Now a design concept of glass envelopes of gas-discharging tubes, which is the basis of the present invention, is described here. The inventors of the present invention had already commercialized a UVC2 surface-emitting light source device with a peak of around 260 nm, and have experimentally developed an ultraviolet light source device using a new deep ultraviolet phosphor with a peak of around 228 nm applied to conventional borosilicate glass (BS1) tubules used as envelopes of UVC2 light-emitting tubes. However, as will be described below with reference to FIG. 9, the transmissivity of the conventional glass BS1 was sharply reduced in a wavelength region of 250 nm and lower, resulting in only weak luminescence intensity.

On the other hand, when new borosilicate glass (BS2), which was experimentally developed based on various experimental results, was used, the ultraviolet light transmissivity in the short wavelength region was greatly improved. As shown in curve G in FIG. 9, an emission spectrum with sufficient intensity was able to be obtained that allowed for transmission of ultraviolet light of 250 nm and lower. However, if the ultraviolet light transmissivity is excessively increased, vacuum ultraviolet light generated by the gas discharge inside the tubes penetrates the glass envelopes; and ultraviolet light with a wavelength around 180 nm is also emitted simultaneously. The emission from the vacuum ultraviolet region, which is generated by the gas discharge, decomposes the ambient air and contributes to the generation of ozone that is expected to purify the air. However, the ozone thereby generated may be toxic depending on an environment in which the ozone is used; and thus this ozone is not necessarily desirable.

In order to achieve optimal bacteria elimination effects, it is necessary to realize glass envelopes that are capable of allowing ultraviolet rays of 250 nm or less to pass therethrough sufficiently, and also hindering the radiation of vacuum ultraviolet rays that are involved in the generation of ozone. The inventors of the present invention thus conducted various experiments on the relationships among materials, thicknesses, and transmissivities of UV transmitting glass that forms envelopes of gas-discharging tubes. The inventors then obtained borosilicate UV-transmitting glass (which were available on the market) with a thickness of 0.6 mm, which are more permeable to UV light than the traditional glass, and analyzed the transmissivity of the borosilicate UV-transmitting glass. The transmissivity of the original tubes of the new borosilicate glass (BS2), shown by a dotted line F in FIG. 9, was still low at around 70% in the vicinity of 228 nm; and as the wavelength became shorter, the transmissivity rapidly became worsened and resulted in 50% or lower at 210 nm. In light of this, the conditions of the tubules were adjusted, forming gas-discharging tubes having glass envelopes with a thin thickness of about 90 μm by using the same glass as the original tubes. As a result, only very limited vacuum ultraviolet light emitted outside the tubes was observed; and 90% or more of the ultraviolet light transmission was achieved at 228 nm. In other words, by using the new borosilicate glass as the new glass enclosure material and controlling the tube thickness, it was confirmed that the transmissivity on the short wavelength side of the emitted ultraviolet light can be selected.

Advantageous Effects of the Invention

The present invention utilizes the gas-discharging tube array-type surface-emitting ultraviolet light source device characterized in that this device does not use highly toxic KrCl gas and environmentally problematic mercury as light sources of deep ultraviolet light at a wavelength (222 nm) beneficial for virus inactivation, thereby obtaining an ultraviolet radiation apparatus that is overall safe to handle. The light emission of the deep ultraviolet phosphor used has a wide emission spectrum in a wavelength region of 240 nm or below that is highly sensitive not only to a single virus but also to many kinds of bacteria, enabling more efficient and wider bacteria elimination/disinfection effects.

Furthermore, the surface-emitting ultraviolet light source device of the present invention is capable of emitting vacuum ultraviolet (VUV) light simultaneously with deep ultraviolet 1 (UVC1). Therefore, this device can generate ozone by decomposing the air circulating in the ozone generation space between the light emitting surfaces and the optical filter with the vacuum ultraviolet VUV, and can utilize both the bacteria elimination effects and the deodorization effects of the ozone.

DETAILED DESCRIPTION OF THE INVENTION

In the following, this invention will be described in detail through the use of the drawings. The following descriptions should be recognized as exemplifications in all respects, and should not be interpreted to limit this invention.

Basic Structure and Drive Principle of Surface-Emitting Ultraviolet Light Source Device A gas-discharging tube array of the present invention used as a surface-emitting ultraviolet light source device is basically the same as the structure disclosed in the above-listed PTL 2, except for a phosphor and a material for glass tubes used for the gas-discharging tube array.

Gas-Discharging Tubes

Figure 1:
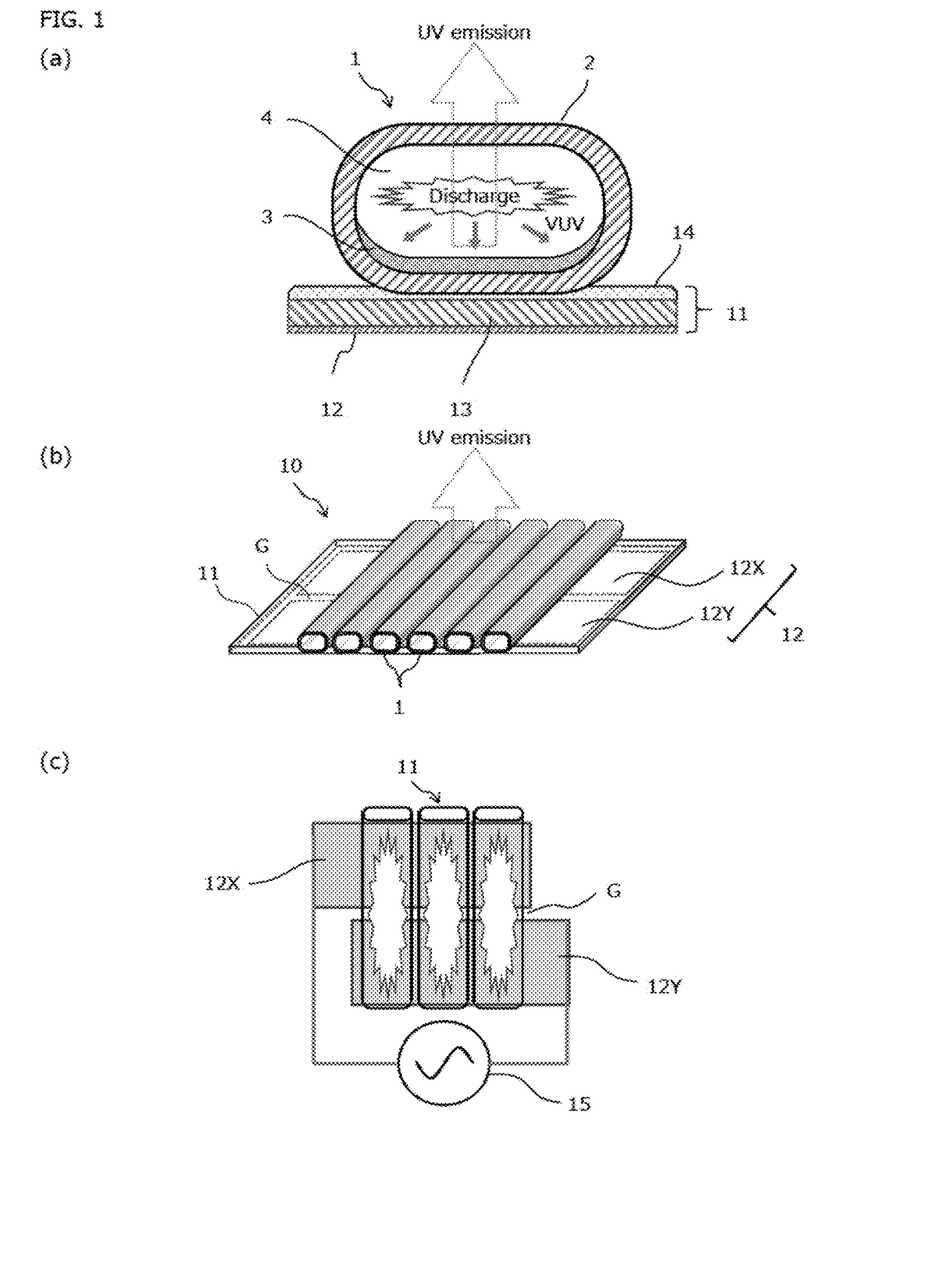
FIG. 1 shows diagrammatic views of configurations of a gas-discharging tube array-type surface-emitting ultraviolet light source device.

FIG. 1(a) shows a transverse cross-section view of a gas-discharging tube that functions as a deep ultraviolet light-emitting element. A gas-discharging tube 1 is mainly formed of a glass tubule 2 having a flat-oval cross-section with a major axis of about 2 mm and a minor axis of about 1 mm as an example, and has a deep ultraviolet phosphor layer 3 on an inner surface thereof on the rear surface side. Also, the gas-discharging tube is configured to enclose a discharge gas 4 containing a mixed gas of noble gases that emit vacuum ultraviolet light, such as neon (Ne) and xenon (Xe), He and Xe, or Ar and Xe, therein, and is configured such that both sides of the gas-discharging tube are sealed.

For the glass tubule 2, inexpensive borosilicate-based glass is used when generating UVC only, while borosilicate-based glass to which a minute amount of fluorine or the like is added is used when generating VUV and UVC simultaneously so as to improve ultraviolet light transmissivity. More specifically, it is suitable to use ultraviolet permeable glass containing a borosilicate-based material, as disclosed in PTL 3. Quartz glass may be used, which is excellent in ultraviolet light permeability, even though it is expensive as a matter of course. By thinning the borosilicate-based glass tube to be 200 μm or less in thickness, preferably up to about 100 μm, by drawing (redrawing), it is possible to obtain the glass tubule 2 that transmits ultraviolet with a transmittance of 80% or higher from a vacuum ultraviolet region with a wavelength of about 140 nm to a deep ultraviolet region with a wavelength of about 280 nm. The tubule with a thickness of 50 μm or less is not desirable because the strength thereof becomes insufficient, possibly leading to breakage.

Figure 2:
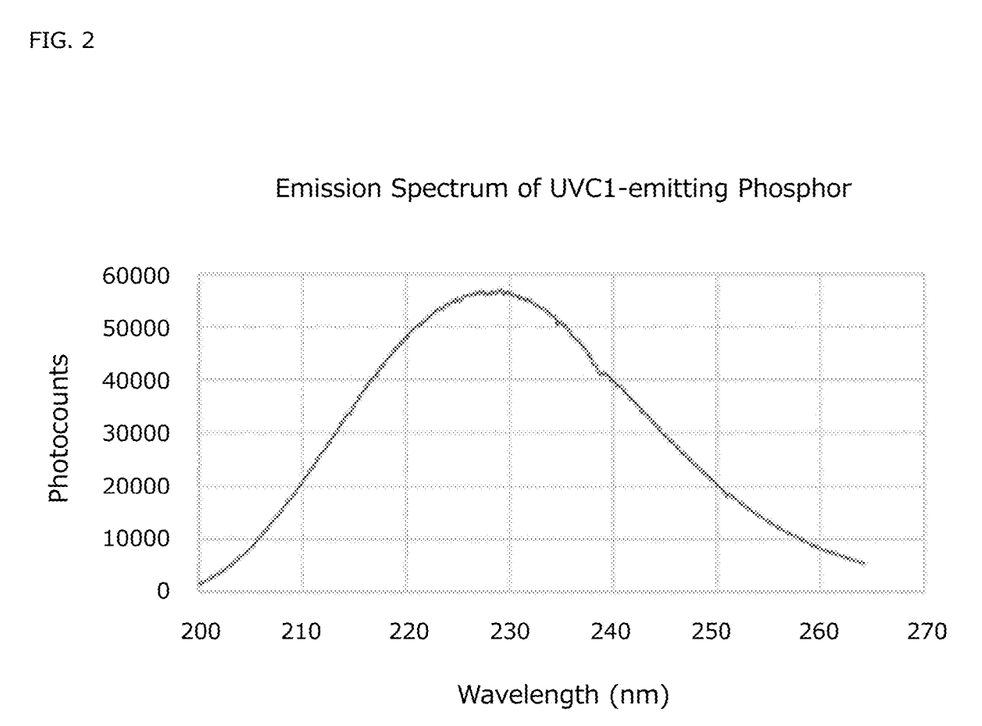
FIG. 2 shows a line drawing indicating a phosphor emission spectrum formed in gas-discharging tubes.

As the deep ultraviolet phosphor layer 3 that is newly used for the present invention, a phosphor is used that comprises phosphate of lutetium and scandium having an emission spectrum peak in the vicinity of a wavelength of 228 nm, such as the one disclosed in PTL 4. The emission spectrum of the phosphor used for the present invention has a continuous and wide wavelength width from 200 nm to 260 nm with a peak of 228 nm and emits deep ultraviolet light that is effective in a range from at least 210 nm to 250 nm, as shown in FIG. 2 as an example.

Surface-Emitting Ultraviolet Light Source Device

A gas-discharging array-type surface-emitting ultraviolet light source device 10, as shown in FIG. 1(b), is formed such that a plurality of gas-discharging tubes 1 as ultraviolet light-emitting elements are arranged in parallel with each other on an electrode substrate 11 having a pair of electrodes 12 (a pair of an electrode 12X and an electrode 12Y). The electrode substrate 11 comprises, for example, a polyimide-based insulating substrate 13 as a main body; an adhesive layer for supporting an array of the gas-discharging tubes 1 thereon; and the pair of electrodes 12 that are placed on a lower surface of the substrate and opposite to the adhesive layer. Another configuration may have the pair of electrodes 12 on an upper surface of the insulating substrate 13 and the adhesive layer as an insulating layer on the electrodes to support the array of the gas-discharging tubes. The pair of electrodes 12 is formed of the electrode 12X and the electrode 12Y that face a bottom surface of each of the gas-discharging tubes 1 and have a pattern in which the electrodes are configured to spread toward both sides of an electrode slit (electrode gap G) interposed between the electrodes.

If the insulating substrate 13 as the main body of the electrode substrate 11 is made of a polyimide resin-based insulating film and is configured to have gas-discharging tubes being aligned in parallel with each other and having clearances therebetween, it is possible to configure the flexible surface-emitting ultraviolet light source device 10 that is curvable as a whole in a tube array direction. If the electrode substrate 11 is configured to have a ventilation hole or a ventilation slit that penetrates through the electrode substrate so as to partially expose bottom surfaces of the gas-discharging tubes 1, this effectively allows for heat release from each gas-discharging tube 1.

Drive Principle

FIG. 1(c) shows a schematic view to describe a drive principle. An inverter circuit 15 applies an alternating drive voltage to the electrode X and the electrode 12Y, which constitute the pair of electrodes 12, at a peak-to-peak voltage (P-P voltage) of 1,000 to 2,000 V at a frequency from 30 to 40 kHz. An initial discharge is generated at a discharge gap inside the gas-discharging tubes 1, which is comparable to the electrode gap G between the electrode 12X and the electrode 12Y, during an increasing process of the alternating drive voltage to be applied by the inverter circuit 15. Following the initial discharge, a discharge expands in a longitudinal direction of the gas-discharging tubes 1 with a subsequent increase of the alternating drive voltage.

By applying the alternating drive voltage, such a discharge occurs repeatedly as alternating polarity of a storage charge in areas within the gas-discharging tubes 1, where correspond to the electrodes 12X, 12Y. In a case where a mixed gas of neon (Ne) and xenon (Xe) is enclosed in the gas-discharging tubes, a discharge is generated with the emission of vacuum ultraviolet (VUV) rays of 143 nm and 172 nm at a low discharge voltage compared to other gases. This VUV excitation causes the phosphor layer 3 to radiate deep ultraviolet (UVC1) having a central wavelength of 228 nm. This drive principle and the specific driving circuit are described in detail in the above-mentioned PTL 2.

Embodiment 1

First Embodiment of the present invention will be described in detail below with reference to the drawings.

FIG. 2 shows a line drawing indicating an emission spectrum from the phosphor layer 3 in deep ultraviolet of the above gas-discharging tube array-type surface-emitting ultraviolet light source device 10. The vertical axis indicates the number of emission photons (photocounts) as luminescence intensity, and the horizontal axis indicates wavelengths. This emission spectrum clearly shows that luminescence intensity of 70% or more at a peak wavelength of 228 nm can be obtained in a continuous wavelength range from 215 to 245 nm.

Figure 3:
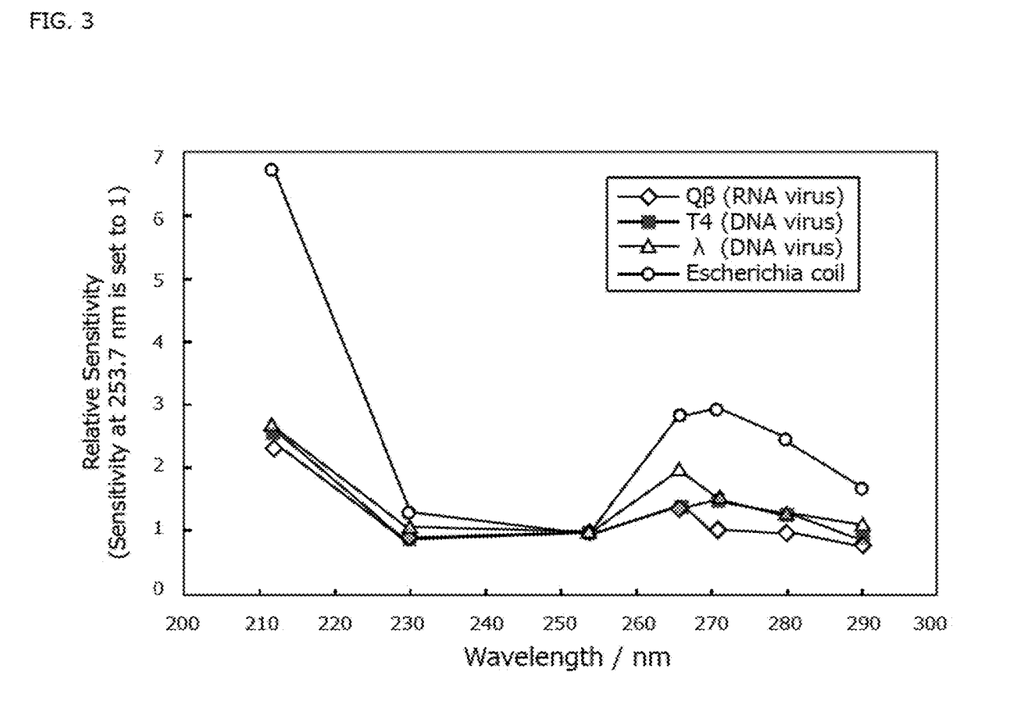
FIG. 3 shows line drawings indicating ultraviolet wavelength sensitivities of viruses and a bacterium.

FIG. 3 shows line drawings indicating the wavelength sensitivities of various viruses and *Escherichia coli* as published in Newsletter No. 4 issued by the Japan UV Water Treatment Technology Association in January 2011. It is found from the line drawings that the UV sensitivities of the various viruses and the bacterium increase on the short wavelength side of 230 nm or less. More specifically, irradiation with broad deep ultraviolet light from the above-described ultraviolet phosphor layer 3 achieves a higher disinfection effect against many bacteria and viruses than irradiation with a single wavelength of 222 nm from a KrCl excimer lamp.

Figure 4:
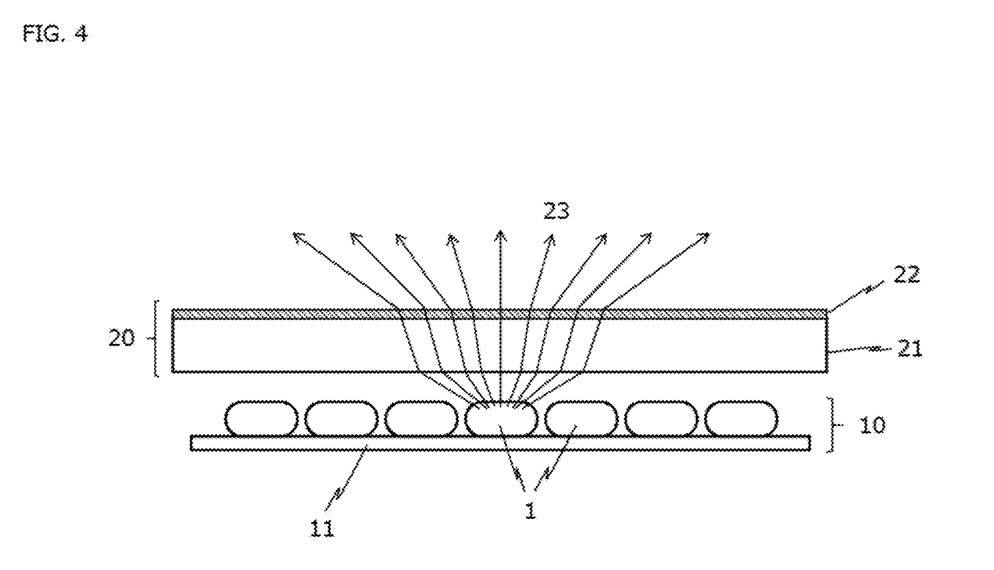
FIG. 4 shows a cross-section view of a structure of an ultraviolet radiation apparatus in accordance with First Embodiment of the present invention.
Figure 5:
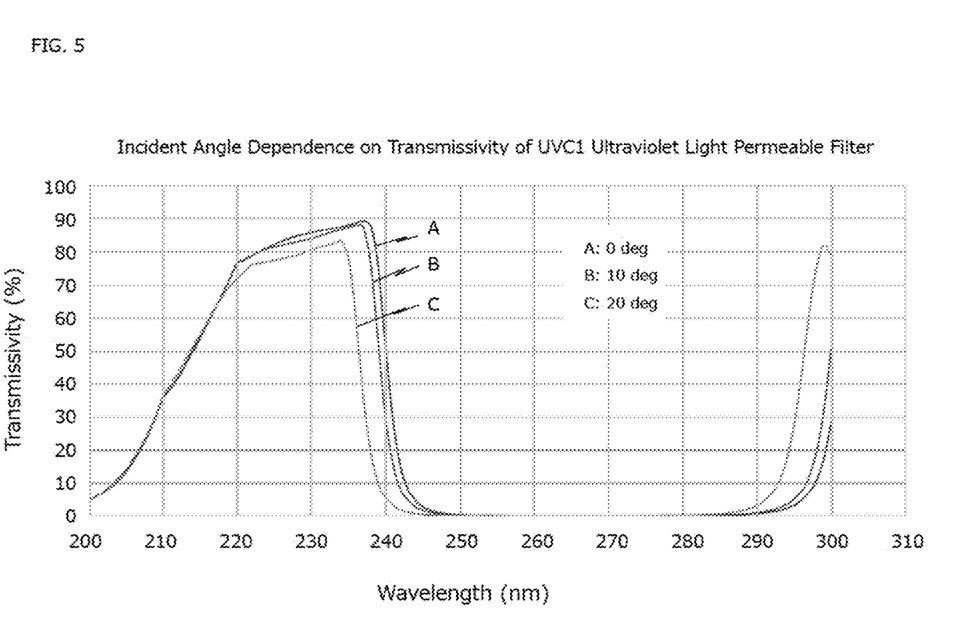
FIG. 5 shows line drawings indicating transmission characteristics and incident angle dependence of an optical filter.

FIG. 4 shows a cross-section view of a basic structure of an ultraviolet radiation apparatus of the present invention in which a surface-emitting ultraviolet light source device 10 having an emission spectrum as shown in FIG. 2 above is assembled with an optical filter 20. The optical filter 20 comprises a synthetic quartz substrate 21 having desirably a thickness of about 1 mm, which is a UV permeable substrate, and a dielectric multilayer filter 22, which is made of $HfO_2/SiO_2$, formed on the above substrate; and this filter has transmission characteristics, which is shown in FIG. 5 with use of a solid line A. More specifically, the optical filter is characterized by transmitting deep ultraviolet rays of 230 nm or lower, including a peak wavelength of 228 nm of the phosphor layer 3, and blocking the transmission of ultraviolet rays of 240 nm or higher, which have a high potential to harm human tissue.

The deep ultraviolet light from the gas-discharging tube array 10 to be used as a light source in the present invention has a wide radiation angle. On the other hand, the dielectric multilayer filter 22 to be assembled with the surface-emitting ultraviolet light source device 10 has incident angle dependence as shown in FIG. 5. In FIG. 5, an angle reference is incidence from a direction perpendicular to a surface of the dielectric multilayer filter 22. Compared to a transmission characteristic at an incident angle of 0 (zero) degrees shown by the solid line A, a transmission characteristic of a radiant ray at an incident angle of 10 degrees is as shown by a dotted line B. For radiant light with an incident angle of 20 degrees, a transmission curve tends to shift toward the shorter wavelength side as an incident angle increases, as shown using a dashed line C. More specifically, in the configuration where radiant light from the surface-emitting ultraviolet light source device 10 is directly incident on the dielectric multilayer filter 22, a peripheral portion of ultraviolet light emitted at a wide angle results in insufficient transmission through the filter.

In the present invention, in order to ensure that deep ultraviolet radiant light from the surface-emitting ultraviolet light source device 10 passes through the dielectric multilayer filter 22 as efficiently as possible, the filter is arranged in combination with the quartz substrate 21 positioned on the incident side of the filter. More specifically, in such an arranged configuration, the quartz substrate 21 in front of the dielectric multilayer filter 22 functions as an optical element that converts the incident angle light rays emitted to the optical filter 20 at a wide radiation angle among the deep ultraviolet rays emitted from each gas-discharging tube 1 at a wide angle. In FIG. 4, the refraction of radiant light rays from a light emitting surface of the gas-discharging tube 1 to the dielectric multilayer filter 22 is shown by arrow lines 23. The radiant light rays from the light emitting surfaces of the gas-discharging tubes 1, which constitute the surface-emitting ultraviolet light source device 10, enter the dielectric multilayer filter 22 with modified radiation angles in directions where the incident angles are narrowed due to a difference between a refractive index (air n≈1) of a space, which is between the radiant light and the quartz substrate 21, and a refractive index (n=1.5) of the quartz substrate. As a result, attenuation of emanating power of the deep ultraviolet light having a central wavelength of 228 nm emitted through the optical filter can be suppressed.

To further reduce loss of incidence of the deep ultraviolet radiant light 23 emitted at a wide angle from the surface-emitting ultraviolet light source device 10 to the dielectric multilayer filter 22, stripes or ribs in a lattice pattern that function as a diffraction grating may be provided on the incident surface side of the quartz substrate 21 constituting the optical filter 20. The stripe ribs corresponding to an array pitch of the gas-discharging tubes 1 are capable of narrowing the incident angle of the deep ultraviolet light emitted from each gas-discharging tube of the surface-emitting ultraviolet light source device 10 at a wide angle to the dielectric multilayer filter 22.

Figure 6:
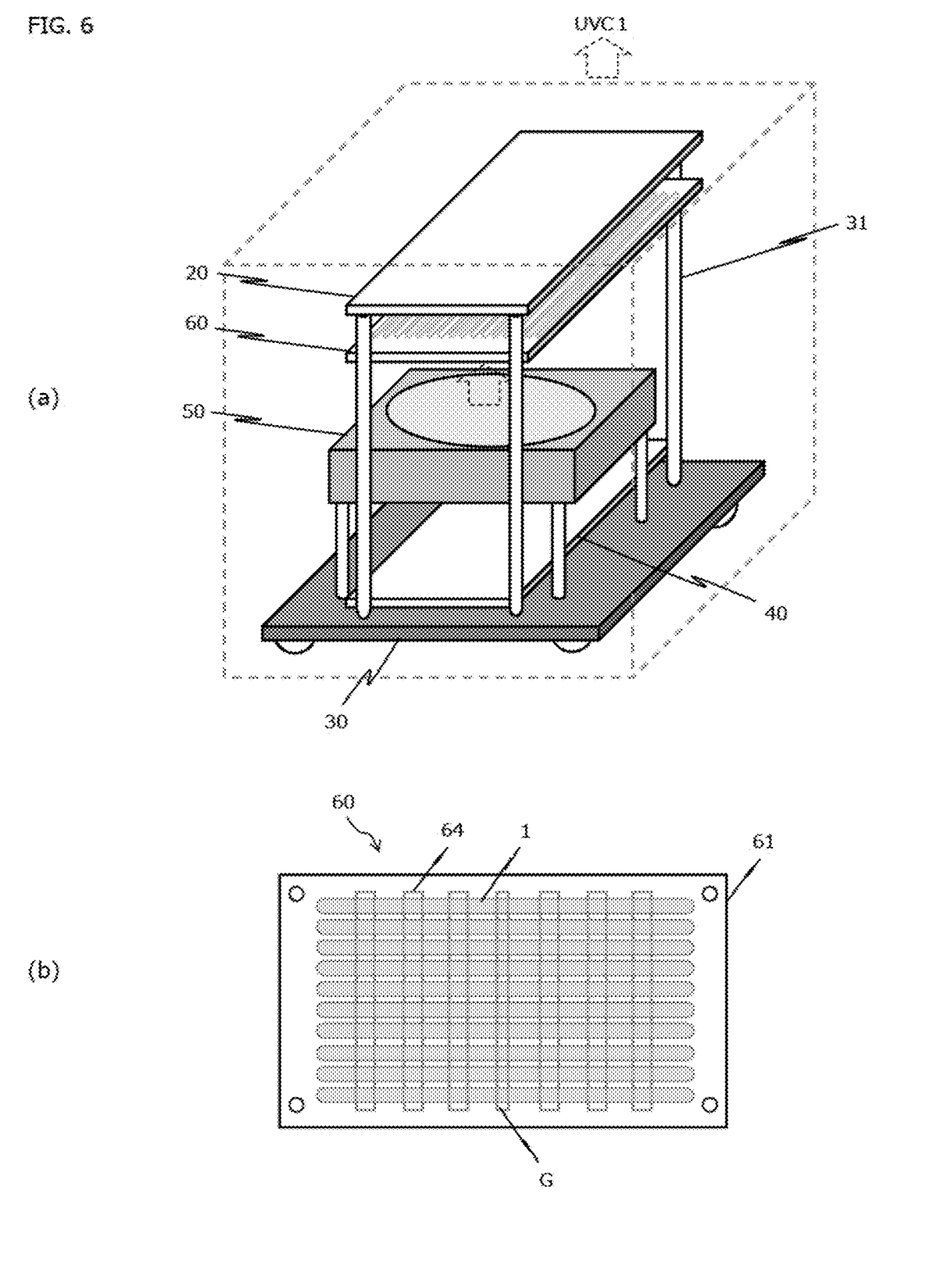
FIG. 6 shows diagrammatic views of assembly configurations of the ultraviolet radiation apparatus in accordance with First Embodiment.

FIG. 6(a) shows a diagrammatic perspective view of an assembly configuration of an ultraviolet radiation apparatus in accordance with Embodiment 1. In this apparatus, a drive circuit board 40 is placed on a base substrate 30 with air inlet holes (not shown); and an air-blowing fan 50, a surface-emitting ultraviolet light source device 60, and an optical filter 20 are assembled above and supported by the base substrate with the use of four (4) columns 31. The whole structure is placed in a housing shown as a dotted diagram, with an ultraviolet irradiation window (aperture) at the top. In FIG. 6, for convenience, the surface-emitting ultraviolet light source device 60 is arranged so that its light emitting surface is configured to be nearly horizontal, and also that UV radiation is directed upward; however, a direction of the UV radiation can be determined arbitrarily.

For the above-described surface-emitting ultraviolet light source device 60, an electrode substrate 61 is used having slits as shown in FIG. 6(b). More specifically, unlike the electrode substrate 11, which has been described above with reference to FIG. 1(b), the electrode substrate 61 shown in FIG. 6(b) has a plurality of through-slits 64 that are arranged almost in parallel with a gap G functioning as a discharge gap and that penetrate through the electrode substrate 61. Such an electrode substrate 61 with the slits is configured in such a way that bottom surfaces (rear surface side) of an array of the gas-discharging tubes 1 are partially exposed downward and that ventilation holes are formed at intersections between clearances formed between the adjacent gas-discharging tubes and the through-slits 64. This configuration allows cooling air from the air-blowing fan 50 to flow through the ventilation holes and thus is capable of effectively cooling the surface-emitting ultraviolet light source device 60. The ventilation holes formed in the electrode substrate may be configured not only to be in the form of slits as described above but also to be in the form of numerous small holes that are configured to partially expose the rear surface side of the discharging tubes.

Embodiment 2

Figure 7:
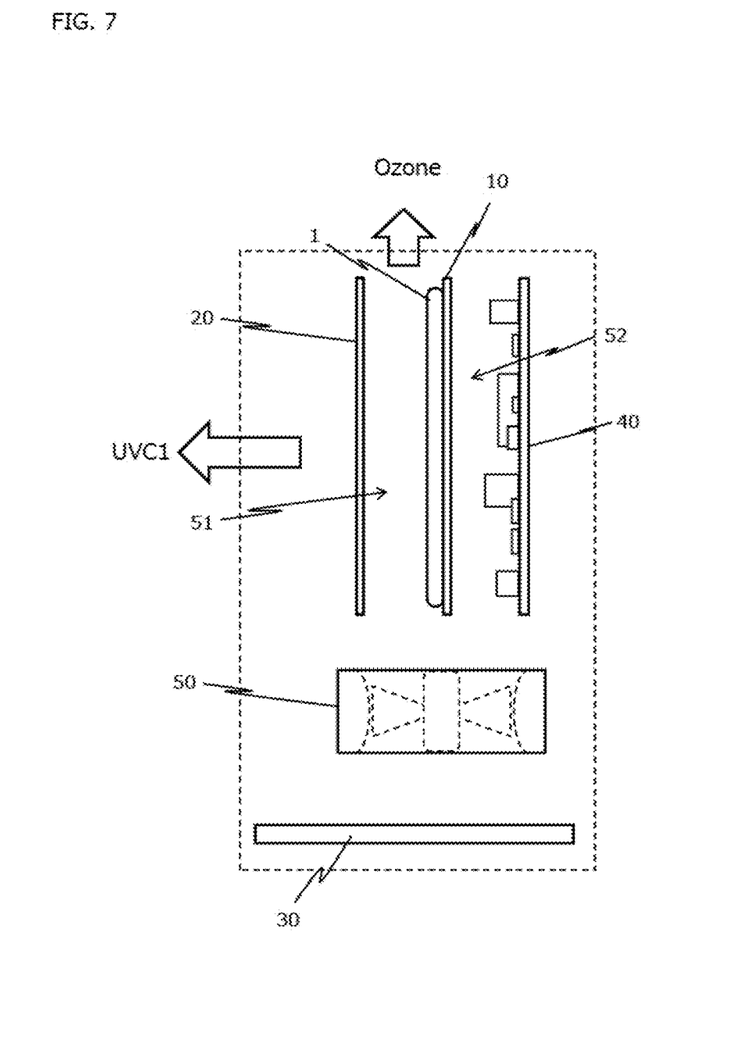
FIG. 7 shows a diagrammatic structural view of an ultraviolet radiation apparatus in accordance with Second Embodiment of the present invention.

FIG. 7 shows a diagrammatic view of a structure of an ultraviolet radiation apparatus in accordance with Second Embodiment of the present invention, in which ozone is generated. The base substrate 30 with the ventilation holes (whose drawings are omitted) is configured to support an assembly configuration in which the optical filter 20 and the drive circuit board 40 are arranged to interpose the gas-discharging tube array-type surface-emitting ultraviolet light source device 10 from the right and left sides. The surface-emitting ultraviolet light source device 10 and the optical filter 20 have a space formed therebetween that functions as an ozone generation space 51. The surface-emitting ultraviolet light source device 10 and the drive circuit board 40 have a space formed therebetween that functions as a heat-releasing passage 52. The air-blowing fan 50 is provided opposite one end of the ozone generation space 51 and the heat-releasing passage 52 each so that an air blow from the air-blowing fan 50 allows ozone to be discharged from the ozone generation space 51 and also simultaneously allows heat generated from the gas-discharging tube array 10 and the drive circuit board 40 to be released from the heat-releasing passage 52.

Figure 8:
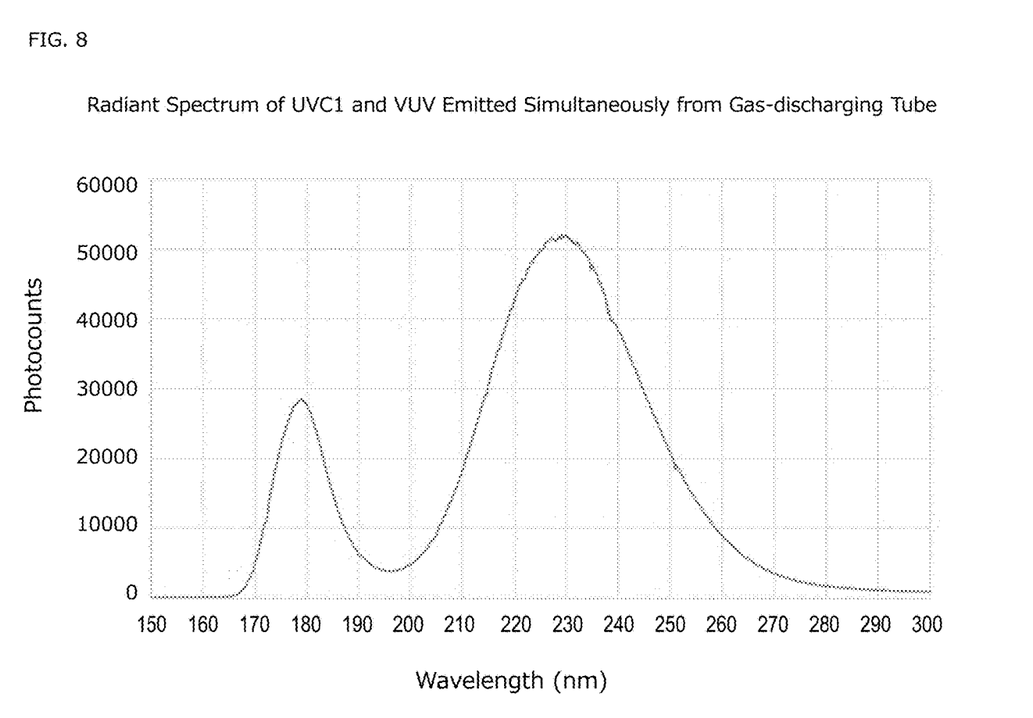
FIG. 8 shows a line drawing indicating an emission spectrum containing VUV and UVC of a surface-emitting ultraviolet light source device in accordance with Second Embodiment.

Owing to the above configuration, each of the gas-discharging tubes 1, which constitute the surface-emitting ultraviolet light source device 10 and are made of the quartz glass tubules 2 or the thin borosilicate glass tubules 2 that are high in ultraviolet light permeability, as described above with reference to FIG. 1, is capable of emitting a deep ultraviolet emission spectrum (UVC1) having a wavelength width at least from 210 nm to 250 nm with a peak wavelength of about 228 nm of the phosphor layer 3 and also simultaneously emitting 172 nm of vacuum ultraviolet (VUV) light. FIG. 8 shows a radiant spectrum of UVC and VUV from the gas-discharging tube array-type surface-emitting ultraviolet light source device used in the above Embodiments.

The drive circuit board 40 is equipped with a timer for controlling irradiation time and a control circuit for controlling the whole device in addition to a drive circuit including the inverter circuit 15 that is to supply an alternating drive voltage to the surface-emitting ultraviolet light source device. The surface-emitting ultraviolet light source device 10 driven by the drive circuit allows deep ultraviolet light of 240 nm or less with a peak wavelength of about 228 nm to irradiate through the optical filter 20 and to subject air in an irradiation space and/or a target object to bacteria elimination and disinfection.

Of vacuum ultraviolet rays generated in the gas-discharging tubes 1, vacuum ultraviolet rays with a wavelength of 172 nm from xenon gas that are reflected from the phosphor layer 3 having an ultraviolet reflection function and are emitted from the light emitting surfaces generate ozone by breaking down air in the ozone generation space 51 between the light emitting surfaces of the gas-discharging tubes 1 constituting the surface-emitting ultraviolet light source device 10 and the optical filter 20. The ozone thereby generated is exhausted with air blown by the air-blowing fan 50 upward, and exhibits a bactericidal action on the ambient air. Naturally, ozone itself has strong oxidation and toxicity and thus is greatly effective for bacteria elimination and disinfection in an unmanned enclosed space regardless of the concentration of the ozone; however, ozone must be limited from excess release into a manned environmental space. In other words, ozone in low concentration is harmless to the human body and is of great use to spatial bacteria elimination.

Therefore, ozone to be released into a manned space needs to be limited in concentration so as not to exceed a reference value of 0.1 ppm, which regulates ozone concentration. For example, the surface-emitting ultraviolet light source device 10 whose light emitting area is 8×3 cm in which twelve (12) gas-discharging tubes having a length of 8 centimeters are arranged is capable of generating 20 mg of ozone per hour. Such an amount of ozone thereby generated from the surface-emitting ultraviolet light source device is capable of not only intermittently applying an alternating drive voltage and changing a duty ratio of the alternating drive voltage so as to appropriately control the amount of ozone but also controlling the drive by turning the drive on and off with feedback from a monitored value of the ozone concentration in the ambient space.

Embodiment 3

In Embodiment 2 above, the device with the following structure is described: the ultraviolet light in the deep ultraviolet region is emitted simultaneously with the vacuum ultraviolet light to generate ozone so that both ozone and UVC1 are used; however, there are some cases where the generation of ozone may not be desirable depending on an environment in which the device is used. The inventors of the present invention have confirmed that the emission of the vacuum ultraviolet light into the outside due to the xenon (Xe) gas discharge can be controlled by the thickness of the glass tube envelopes. More specifically, glass tubes made of synthetic quartz are unable to adjust ultraviolet light transmissivity by the glass thickness, whereas tubes made of borosilicate-based ultraviolet-permeable glass are capable of increasing ultraviolet light transmissivity of ultraviolet rays with a same wavelength by thinning the glass tubes and simultaneously capable of shifting toward the short wavelengths.

Figure 9:
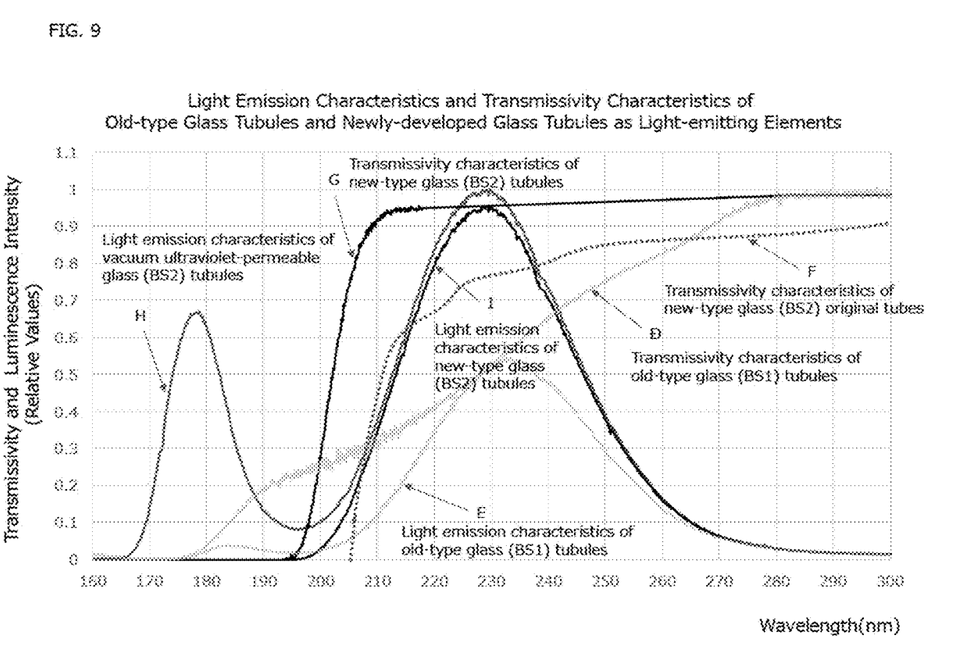
FIG. 9 shows line drawings indicating relationships between light emission characteristics of gas-discharging tubes and ultraviolet permeation characteristics of glass tubes.

FIG. 9 shows line drawings indicating relationships between ultraviolet light transmissivities of borosilicate-based ultraviolet-permeable glass tubes, which are available in the market, and ultraviolet radiant spectrums. A curve D indicates an ultraviolet light transmissivity characteristics of old-type borosilicate glass (BS1) tubes that conventionally emit an ultraviolet ray of 260 nm. A device formed of this glass and a phosphor with 228 nm emits an emission waveform of a curve E. Such a device is incapable of sufficient ultraviolet light emission within a range of 210 to 250 nm. In the meanwhile, a curve F is a transmissivity curve exhibited by a glass-based material tube having a diameter of 15.7 mm and a thickness of 0.6 mm, which was obtained in the market as a borosilicate-based ultraviolet-permeable glass tube (BS2); and this curve shows that an ultraviolet light transmissivity drops toward the short wavelength side at a wavelength of 220 nm with a transmissivity of about 70%, and a cut-off wavelength is about 205 nm. The glass-based material tube drawn (redrawn) into a tube having a flat-oval cross-section with a major axis of 2.5 mm, a minor axis of 1 mm, and a thickness of 90 μm has exhibited a transmissivity characteristic shown as a curve G.

In FIG. 9, a curve H is a radiant spectrum of the vacuum ultraviolet light and the deep ultraviolet light radiated from the phosphor layer that are previously shown in FIG. 8; and this characteristic can be obtained by the gas-discharging device configured to comprise quartz glass tubes or the above-described vacuum ultraviolet-permeable borosilicate-based glass tubes (BS2) whose thickness is reduced to 70 μm or less. A curve I, however, shows a light emission characteristic obtained by gas-discharging tubes comprising the same deep ultraviolet phosphor layer configured to have the borosilicate glass tubes (BS2) with a thickness of 90 μm and having the transmissivity characteristic of the above-described curve G. It is found from these light source devices having such structures that the emission within a vacuum ultraviolet region having a peak at around 178 nm is cut off, and ultraviolet emission within a broad band from 200 to 260 nm is obtained.

Figure 10:
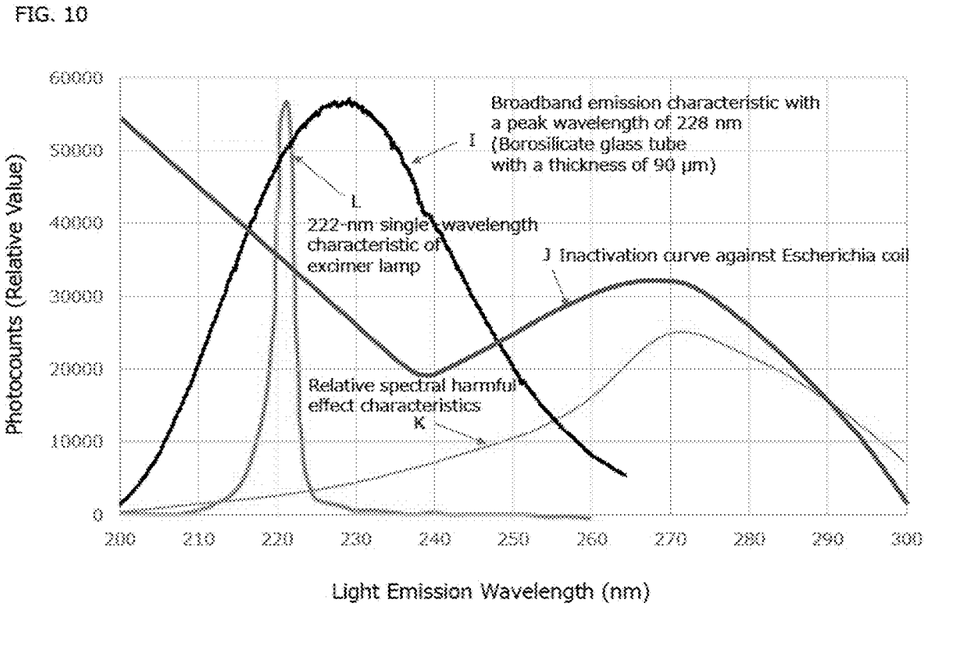
FIG. 10 shows line drawings indicating relationships of light emission wavelength characteristics of the ultraviolet light source device of the present invention to inactivation curves and relative harmful effect characteristics of ultraviolet light on the bacterium.

FIG. 10 shows a characteristic that is the same as the broadband emission characteristic curve shown in FIG. 2 emitted from the deep ultraviolet phosphor layer with a peak wavelength of 228 nm (which is the same as the curve I shown in FIG. 9) together with an inactivation curve J against a bacterium and a relative spectral harmful characteristic curve K. The inactivation curve J against the bacterium shares the same source with the line drawings shown in FIG. 3 indicating the wavelength sensitivities of *Escherichia coli* and others; and the relative spectral harmful characteristic K is widely known, as provided for in the Japanese Industrial Standards (JIS) (Z8812-1987). As is evident from this line drawing, the inactivity against the bacterium is prone to increase from a wavelength of about 240 nm toward the short wavelength side, while hazardous effects on the human body are prone to decrease from a wavelength of 270 nm toward the short wavelength side. Given this relationship, it is well understood that the deep ultraviolet light with a wide wavelength width from 200 nm to 240 nm holds down the hazardous effects, thereby extensively realizing disinfection actions. A curve L is shown here for comparison, which indicates a 222-nm single-wavelength characteristic of an excimer lamp using a KrCl gas disclosed in PTL 1 and is perceived to have a limitation on bacterial inactivity.

Other Modified Examples

The above are the representative structural examples of the present invention; however, there are various other modified examples available. For instance, a gas-discharging tube array-type surface-emitting ultraviolet light source device is characterized by being mercury-free and also characterized by having an electrode substrate adapted to be flexible, thereby enabling the device to be bendable in a tube array direction. Therefore, the light emitting surfaces of the surface-emitting ultraviolet light source device 10 can be configured to be concavely bended; and also the incident side of the optical filter 20 is configured to be concaved, thereby allowing light rays for irradiating a target object to be converged, and increasing irradiation intensity. Alternatively, an optical element, such as a lenticular lens, made of an ultraviolet permeable material, instead of the above-described optical filter, may be placed in front of the concavely-bended light source device so that more irradiated light rays are converged.

When the irradiation of the deep ultraviolet light is carried out simultaneously with the elimination of bacteria in the air by generating ozone, as in Embodiment 2, the plurality of gas-discharging tubes constituting the surface-emitting ultraviolet light source device 10 may not necessarily have a same emission spectrum. The device may be configured to have a hybrid array configuration such that gas-discharging tubes that are exclusive to vacuum ultraviolet irradiation to form an ultraviolet light reflection layer made of magnesium oxide (MgO), aluminum oxide ($Al_2O_3$), or the like, instead of the phosphor layer 3, are interposed and arranged between deep ultraviolet irradiation gas-discharging tubes. Alternatively, a gas-discharging tube array-type light source device with a super broad band and flat luminescence intensity can be configured by digestedly disposing and arranging gas-discharging tubes using a phosphor with peak wavelengths of 191 nm and 209 nm as disclosed in, for example, PTL 4 between the above-described gas-discharging tubes using the above-described broad band-emitting phosphor with the peak wavelength of 228 nm as the material for the deep ultraviolet phosphor layer 3. By assembling this device with an optical filter that cuts off wavelengths of 240 nm or more, an ultraviolet radiation apparatus can be obtained whose harmful effects are low and that exerts a wide range of inactivation effects against viruses and bacteria.

If a broadband deep ultraviolet phosphor material that does not substantially have an emission spectrum ingredient of 240 nm or more but has a central wavelength at 228 nm is used as the phosphor layer 3 or if a radiation apparatus whose emission wavelength spectrum exceeds 240 nm is prepared to be used in an unmanned environment, the optical filter 20 may be omitted. Alternatively, a protection plate that is simply made of an ultraviolet permeable material may be placed instead of the dielectric multilayer filter 22 so as to form an ozone generation space between the protection plate and the surface-emitting ultraviolet light source device 10.

The present invention can be further developed to prepare an air sterilization apparatus by using the above-described surface-emitting ultraviolet light source device that generates VUV light simultaneously with UVC light by the phosphor. More specifically, the air sterilization apparatus can be prepared by arranging the drive circuit board 40, the air-blowing fan 50, and the VUV+UVC surface-emitting light source device 60, in a similar way to the configuration shown in FIG. 6(a) or FIG. 7, inside a sterilization box provided with a lead-in opening for allowing air, which is to be sterilized, to enter from an ambient environment and a lead-out opening for allowing the sterilized air to be discharged. Without releasing the deep ultraviolet light from the phosphor to the outside, this apparatus is capable of performing bacteria-eliminating action and deodorizing action on the air entered by using ozone generated by VUV in the sterilization box and nascent active oxygen generated by the reaction of the ozone with UVC and also capable of releasing clean air and residual ozone from the sterilization box to the environment. The phosphor layer may be appropriately used that has an ultraviolet reflection function on a coating surface thereof and emits light in a deep ultraviolet region; however, it is preferable to use a UVC2-emitting phosphor with a peak of 260 nm. In this case, the optical filter 20 is unnecessary and thus can be omitted; or a lid having an air-discharging pore may be placed instead.

Moreover, an ultraviolet radiation apparatus can be configured to have large light emitting surfaces by having a plurality of long gas-discharging tubes placed on an electrode substrate having a number of pairs of electrodes, each pair of electrodes being configured to have a discharging electrode gap arranged therebetween, the discharging electrode gaps being arranged in a direction that intersects with a longitudinal direction of the gas-discharging tubes. The size of the light emitting surfaces may be determined by the length of the gas-discharging tubes and the number of the gas-discharging tubes, and also a configuration pattern of the electrode pairs divided by the gaps. Another radiation apparatus with large light emitting surfaces may be configured by tiling a plurality of small-size surface-emitting ultraviolet light source devices.

The surface-emitting ultraviolet light source device may be configured to have an ultraviolet-permeable flat glass enclosure that encloses a deep ultraviolet phosphor layer and ultraviolet light or an electron beam excitation source, both of which generating deep ultraviolet light by the excitation of the phosphor layer. The electron beam excitation source may be used that is configured to emit electrons according to the principle of field emission.

CONCLUSIONS

Whatever the case may be, by virtue of the present invention, all the ultraviolet radiation apparatuses described above can be obtained that have the bacteria elimination/disinfection effects against viruses and bacteria and yet are safe at a minimum of ill effects of ultraviolet light on the human body.

This invention has another aspect that includes any combinations of the above-described aspects.

In addition to the above-described Embodiments, this invention may have a variety of modified examples. It should not be interpreted that these modified examples are excluded from the scope of this invention. The scope of this invention is intended to include the meanings equivalent to the scope of the claims and also include all alterations (and modifications) within the scope of the claims.

REFERENCE SIGNS LIST

1: gas-discharging tube
2: glass tubule
3: phosphor layer
4: discharge gas
G: electrode gap
10, 60: surface-emitting ultraviolet light source device, gas-discharging tube array
11, 61: electrode substrate
12: a pair of electrodes
12X, 12Y: electrode
13: insulating substrate
15: inverter circuit
20: optical filter
21: quartz substrate, synthetic quartz substrate
22: dielectric multilayer filter
23: radiant light, arrow line
30: base substrate
31: column
40: drive circuit board
50: air-blowing fan
51: ozone generation space
52: heat-releasing passage
64: through-slit

The invention claimed is:

1. An ultraviolet radiation apparatus comprising:
gas-discharging tubes for ultraviolet emission arranged in parallel with each other on a pair of electrodes to share the electrodes with each other;
an optical filter placed in front of light emitting surfaces of a light source device that emit ultraviolet light with a wavelength width at least from 210 nanometers (nm) to 250 nm in a deep ultraviolet region, the optical filter substantially blocking the transmission of ultraviolet rays of 240 nm or more of the ultraviolet light; and
glass enclosures constituting the gas-discharging tubes and configured to have a thickness at the front surface side of the glass enclosures in such a way as to limit the emission of the ultraviolet light with wavelengths shorter than a peak wavelength.

2. The ultraviolet radiation apparatus according to claim 1,
wherein the light source device mainly comprises the glass enclosures that have the front surface side serving as the light emitting surfaces and the rear surface side on the opposite side of the front surface side and that are made of UV-transmitting glass;
wherein the glass enclosures each have a phosphor layer provided on an inner surface thereof on the rear surface side of the glass enclosures, the phosphor layer emitting ultraviolet light with a wavelength range at least from 210 nm to 250 nm in a deep ultraviolet region; and
wherein the light source device is provided with: the gas-discharging tubes therein configured to enclose a discharge gas therein that generates vacuum ultraviolet light; and the pair of electrodes that spread toward both sides of a clearance functioning as a discharge gap interposed between the electrodes and face the rear surface side of the gas-discharging tubes.

3. The ultraviolet radiation apparatus according to claim 2, wherein the phosphor layer has a broadband emission spectrum with the peak wavelength of around 228 nm.

4. The ultraviolet radiation apparatus according to claim 1, wherein each of the glass enclosures is made of UV-transmitting glass having a thickness of 70 micrometers (μm) or more at the front surface side of the glass enclosures.

5. The ultraviolet radiation apparatus according to claim 1, wherein the optical filter is made of a dielectric multilayer filter formed on a surface of an ultraviolet permeable substrate; and
wherein the ultraviolet permeable substrate is configured to face the light emitting surfaces of the gas-discharging tubes constituting the light source device, and is configured to regulate incident angles of radiant light from the light emitting surfaces to the dielectric multilayer filter due to a difference between a refractive index of a space, which is between the light emitting surfaces and the ultraviolet permeable substrate, and a refractive index of the ultraviolet permeable substrate.

6. The ultraviolet radiation apparatus according to claim 1, wherein glass tubes constituting the gas-discharging tubes are made of a borosilicate-based UV-transmitting glass-based material and comprise tubules characterized by allowing a wavelength of 220 nm to have an ultraviolet light transmissivity of 70 percent (%)±15% with a thickness of 0.6 millimeters (mm) and by having an ultraviolet cut-off wavelength of 205 nm±5 nm and having a thickness of 70 μm or more at the front surface side of the tubules.

7. The ultraviolet radiation apparatus according to claim 1, wherein glass tubes constituting the gas-discharging tubes are made of borosilicate-based UV-transmitting glass and comprise tubules characterized by allowing a wavelength of 220 nm to have an ultraviolet light transmissivity of 90%±10% with a thickness of 0.07 mm and by having an ultraviolet cut-off wavelength of 200 nm±10 nm and having a thickness of 70 μm or more at the front surface side of the tubules.

8. The ultraviolet radiation apparatus according to claim 1, wherein the optical filter has a dielectric multilayer filter structure formed on the ultraviolet emission surface side of a quartz substrate, and comprises a diffraction grating provided on the ultraviolet incident surface side of the quartz substrate.

9. The ultraviolet radiation apparatus according to claim 1, wherein the optical filter has a dielectric multilayer filter structure formed on the ultraviolet emission surface side of a quartz substrate, and comprises ribs in a stripe pattern provided on the ultraviolet incident surface side of the quartz substrate to narrow incident angles of radiant light from the gas-discharging tubes to the dielectric multilayer filter.

10. The ultraviolet radiation apparatus according to claim 1, wherein the optical filter has a dielectric multilayer filter structure formed on the ultraviolet emission surface side of a quartz substrate, and comprises ribs in a lattice pattern provided on the ultraviolet incident surface side of the quartz substrate to narrow incident angles of radiant light from the gas-discharging tubes to the dielectric multilayer filter.

11. The ultraviolet radiation apparatus according to claim 1, wherein the optical filter has a dielectric multilayer filter structure formed on the ultraviolet emission surface side of a quartz substrate, and comprises a plurality of ribs in a stripe pattern or a lattice pattern provided corresponding to an array of the gas-discharging tubes on the ultraviolet incident surface side of the quartz substrate to narrow incident angles of radiant light from the gas-discharging tubes to the dielectric multilayer filter.

12. An ultraviolet radiation apparatus mainly having a ultraviolet light source device comprising:
   glass enclosures,
      wherein the glass enclosures each have the front surface side serving as light emitting surfaces and the rear surface side on the opposite side of the front surface side and have a phosphor layer therein, the phosphor layer being configured to emit ultraviolet light in a deep ultraviolet light region,
      wherein the glass enclosures each enclose a discharge gas that excites the phosphor layer to generate vacuum ultraviolet light;
   a pair of electrodes having a pattern in which the electrodes are configured to be on the opposite side of the rear surface side of the glass enclosures and to spread toward both sides of a clearance functioning as a discharge gap interposed between the electrodes; and
   an optical filter placed in front of the light emitting surfaces of the ultraviolet light source device and limiting emission wavelengths on the long wavelength side of an emission spectrum of the phosphor layer,
   wherein each of the glass enclosures is made of borosilicate-based UV-transmitting glass and has a thickness of 70 μm or more at the front surface side of the glass enclosures in such a way as to selectively limit, on the short wavelength side of the emission spectrum, the emission of ultraviolet light including vacuum ultraviolet light generated inside the ultraviolet light source device due to the thickness at the front surface side of the glass enclosures.

13. The ultraviolet radiation apparatus according to claim 12, wherein the phosphor layer has the broadband emission spectrum with a peak wavelength of around 228 nm.

14. The ultraviolet radiation apparatus according to claim 12, wherein the optical filter placed in front of the light emitting surfaces of the ultraviolet light source device blocks the transmission of ultraviolet rays of wavelengths of 240 nm or more.

15. The ultraviolet radiation apparatus according to claim 12,
   wherein the optical filter is made of a dielectric multilayer filter formed on a surface of a quartz substrate having a refractive index larger than a refractive index of air; and
      wherein the quartz substrate is configured to face the light emitting surfaces of the gas-discharging tubes constituting the ultraviolet light source device, and is configured to regulate incident angles of radiant light from the light emitting surfaces to the dielectric multilayer filter due to a difference between a refractive index of the quartz substrate and a refractive index of a space, which is between the light emitting surfaces and the quartz substrate.

16. An ultraviolet radiation apparatus having a gas-discharging tube array mainly comprising glass tubules having the front surface side serving as light emitting surfaces and the rear surface side on the opposite side of the front surface side,
   wherein the glass tubules each have a deep ultraviolet phosphor layer provided on an inner surface thereof on the rear surface side of the glass tubules and enclose a discharge gas therein;
wherein the gas-discharging tube array comprises gas-discharging tubes arranged in parallel with each other and a pair of electrodes,
   wherein the pair of electrodes having a pattern in which the electrodes are configured to be on the opposite side of the rear surface side of the gas-discharging tube array and to spread toward both sides of an electrode slit functioning as a discharge gap interposed between the electrodes and shared by the gas-discharging tubes;
   wherein the gas-discharging tubes each have an optical filter placed in front of the gas-discharging tubes on the front surface side;
   wherein the optical filter is provided with a diffraction grating on the incident surface side to substantially block the transmission of ultraviolet rays of 240 nm or more of an emission spectrum of the phosphor layer; and
   wherein each of the glass tubules is made of glass having a thickness of 70 μm or more.

17. The ultraviolet radiation apparatus according to claim 16, wherein the phosphor layer has the broadband emission spectrum with a peak wavelength of around 228 nm.

18. The ultraviolet radiation apparatus according to claim 16, wherein the optical filter comprising the diffraction grating has a dielectric multilayer filter structure formed on the ultraviolet emission surface side of a quartz substrate, and comprises the diffraction grating provided on the ultraviolet incident surface side of the quartz substrate, wherein the diffraction grating comprises ribs in a stripe pattern.

19. The ultraviolet radiation apparatus according to claim 16, wherein the optical filter comprising the diffraction grating has a dielectric multilayer filter structure formed on the ultraviolet emission surface side of a quartz substrate, and comprises the diffraction grating provided on the ultraviolet incident surface side of the quartz substrate, wherein the diffraction grating comprises ribs in a lattice pattern.

20. The ultraviolet radiation apparatus according to claim 16, wherein the optical filter comprising the diffraction grating has a dielectric multilayer filter structure formed on the ultraviolet emission surface side of a quartz substrate, and comprises the diffraction grating provided on the ultraviolet incident surface side of the quartz substrate, wherein the diffraction grating is a plurality of ribs in a stripe pattern or a lattice pattern corresponding to an array pitch of the gas-discharging tubes.

* * * * *